US009089409B2

(12) United States Patent
Wu

(10) Patent No.: US 9,089,409 B2
(45) Date of Patent: Jul. 28, 2015

(54) ADJUSTABLE WAIST PAD

(71) Applicant: Ying-Ching Wu, Tainan (TW)

(72) Inventor: Ying-Ching Wu, Tainan (TW)

( * ) Notice: Subject to any disclaimer, the term of this patent is extended or adjusted under 35 U.S.C. 154(b) by 443 days.

(21) Appl. No.: 13/661,099

(22) Filed: Oct. 26, 2012

(65) Prior Publication Data

US 2014/0121578 A1 May 1, 2014

(51) Int. Cl.
*A61F 5/00* (2006.01)
*A61F 5/02* (2006.01)

(52) U.S. Cl.
CPC . *A61F 5/028* (2013.01); *A61F 5/02* (2013.01); *A61F 5/022* (2013.01); *A61F 5/026* (2013.01)

(58) Field of Classification Search
CPC .......................................... A61F 5/028
USPC ............ 602/1, 5, 32, 36, 19, 20; 450/94, 155; D24/188–192; 128/100.1, 101.1, 128/121.1, 96.1; 482/106, 139; 2/338, 44, 2/311, 268, 2, 336
See application file for complete search history.

(56) References Cited

U.S. PATENT DOCUMENTS

| 1,887,486 | A | * | 11/1932 | Quine | 450/128 |
| 1,924,016 | A | * | 8/1933 | Barrows | 602/19 |
| 1,974,283 | A | * | 9/1934 | Kendrick | 602/19 |
| 2,100,964 | A | * | 11/1937 | Kendrick | 602/19 |
| 2,219,475 | A | * | 10/1940 | Flaherty | 602/19 |
| 6,213,968 | B1 | * | 4/2001 | Heinz et al. | 602/19 |
| 2005/0251074 | A1 | * | 11/2005 | Latham | 602/19 |

* cited by examiner

*Primary Examiner* — Alireza Nia
*Assistant Examiner* — Tarla Patel
(74) *Attorney, Agent, or Firm* — Alan D. Kamrath; Kamrath IP Lawfirm, P.A.

(57) ABSTRACT

An adjustable waist pad (2) includes first and second bands (20, 30). An abutment face (36) at a free end (28) of the first band (20) is detachably engaged with an engagement face (38) of the second band (30). Two positioning members (44, 70) are detachably engaged with the engagement faces (24, 38) at engagement ends (26, 32) of the first and second bands (20, 30), respectively. A string (90) is extended through inner ends (46, 72) of two positioning member (44, 70) in a criss-cross manner. Two elastic straps (62, 85) are fixed to the positioning members (44, 70) and detachably engaged with the first and second bands (20, 30). Two fixing members (96, 98) are fixed to two ends of the string (90). A tightening force of the waist pad (2) can be increased by pulling the elastic straps (62, 85).

2 Claims, 13 Drawing Sheets

ADJUSTABLE WAIST PAD

BACKGROUND OF THE INVENTION

The present invention relates to an adjustable waist pad and, more particularly, to an adjustable waist pad allowing adjustment of tightness.

A type of waist pad includes a band including hooks and loops respectively provided on inner and outer faces of the band. If a user is intended to adjust the tightness of the band after the band has been worn on a waist of the user, the user has to disengage the hooks from the loops, move the band, and reengage the hooks with the loops. However, a large contact area between the hooks and the loops is involved in each adjustment, and it is difficult for the user to obtain the desired tightness.

Another type of waist pad includes two bands, with a plate fixed to each of two associated ends of the bands. A plurality of protrusions is provided on each of two associated plates, with two strings wound around the protrusions, with an adjusting member provided on each of two ends of each string. The adjustment members can be moved to pull the bands via the strings, shortening a spacing between the plates. On the other hand, the plates can be moved away from each other to increase the spacing therebetween. Thus, the tightness of the waist pad can be adjusted by adjusting the spacing. However, the bands have a fixed length such that the adjustment of the spacing is limited. If the spacing between the plates is excessively increased, the back of the waist of the user is merely pulled by the strings in the transverse direction, reducing the tightening force while the strings fail to provide support in the vertical direction.

Thus, a need exists for a novel waist pad allowing easy adjustment of tightness.

BRIEF SUMMARY OF THE INVENTION

The present invention solves this need and other problems in the field of easy minor adjustment of waist pads having a large wrapping area by providing an adjustable waist pad including a first band having an engagement end and a free end. The first band further includes an abutment face and an engagement face opposite to the abutment face, with each of the abutment face and the engagement face of the first band extending from the engagement end to the free end of the first band. A second band includes an engagement end and a free end. The second band further includes an abutment face and an engagement face opposite to the abutment face, with each of the abutment face and engagement face of the first band extending from the engagement end to the free end of the second band. The abutment face at the free end of the first band is detachably engaged with the engagement face of the second band.

A first positioning member includes an inner end and an outer end opposite to the inner end. The first positioning member further includes a coupling face and an outer face opposite to the coupling face, with each of the coupling face and the outer face extending from the inner end to the outer end of the first positioning member. Three upper holes are defined in the inner end of the first positioning member and spaced from each other in a vertical direction. The coupling face of the first positioning member is detachably engaged with the engagement face at the engagement end of the first band.

A second positioning member includes an inner end and an outer end opposite to the inner end. The second positioning member further includes a coupling face and an outer face opposite to the coupling face, with each of the coupling face and the outer face extending from the inner end to the outer end of the second positioning member. Three upper holes are defined in the inner end of the second positioning member and spaced from each other in the vertical direction. The coupling face of the second positioning member is detachably engaged with the engagement face at the engagement end of the second band. A spacing is defined between the inner ends of the first and second positioning member. Each of the three upper holes of the second positioning member is aligned with a corresponding one of the three upper holes of the first positioning member.

A first string includes first and second ends. The first end of the first string is extended through the uppermost upper hole of the first positioning member, the middle upper hole of the second positioning member, and the bottommost upper hole of the first positioning member. The second end of the first string is extended through the uppermost upper hole of the second positioning member, the middle upper hole of the first positioning member, and the bottommost upper hole of the second positioning member.

A first elastic strap has a connection end and an engagement end. The connection end of the first elastic strap is fixed to the outer end of the first positioning member. The first elastic strap further includes a coupling face and an outer face opposite to the coupling face, each of the coupling face and the outer face of the first elastic strap extending from the connection end to the engagement end of the first elastic strap. The coupling face at the engagement end of the first elastic strap is detachably engaged with the engagement face of the first band, providing a tightening force.

A second elastic strap has a connection end and an engagement end. The connection end of the second elastic strap is fixed to the outer end of the second positioning member. The second elastic strap further includes a coupling face and an outer face opposite to the coupling face of the second elastic strap, with each of the coupling face and the outer face of the second elastic strap extending from the connection end to the engagement end of the second elastic strap. The coupling face at the engagement end of the second elastic strap is detachably engaged with the engagement face of the second band, providing a tightening force.

A first fixing member is fixed to the first end of the first string and includes a coupling face. A second fixing member is fixed to the second end of the first string and includes an engagement face detachably engaged with the coupling face of the first fixing member.

When the first and second bands are wrapped around a waist of a user, the tightening force of the first and second bands is increased if the first and second ends of the first string are pulled to reduce the spacing between the inner ends of the first and second positioning members.

In the form shown, the first positioning member further includes three lower holes defined in the inner end thereof and spaced from each other in the vertical direction. The lower holes of the first positioning member are located below the upper holes of the first positioning member. The second positioning member further includes three lower holes defined in the inner end thereof and spaced from each other in the vertical direction. The lower holes of the second positioning member are located below the upper holes of the second positioning member. Each lower hole of the second positioning member is aligned with a corresponding lower hole of the first positioning member. A first end of a second string extended through the uppermost lower hole of the first positioning member, the middle lower hole of the second positioning member, and the bottommost lower hole of the first positioning member. A second end of the second string is extended through the bottommost lower hole of the second positioning member, the middle lower hole of the first positioning member, and the uppermost lower hole of the second positioning member. The first end of the second string is fixed to the first fixing member. The second end of the second string is fixed to the second fixing member. When the first and second bands are wrapped around a waist of a user, the tightening force of the first and second bands is increased if the first and second ends of the second string are pulled to reduce the spacing between the inner ends of the first and second positioning members.

In the form shown, the waist pad further includes two clamping members, with each clamping member including a compartment having a first opening and a second opening larger than the first opening. The compartment includes a wall having a sliding groove. A wheel is rotatably mounted in the compartment of each clamping member and includes a pivot formed on a side thereof and extending into the sliding groove of a corresponding clamping member. The pivot of each wheel is slideable in the sliding groove to move the wheel between the first and second openings. Two sections respectively of the first and second strings extend through the compartment of one of the clamping members. Another two sections respectively of the first and second strings extend through the compartment of the other clamping member.

When the wheels are located adjacent to the first openings of the clamping members, the two sections of the first and second strings are clamped between one of the wheels and one of the clamping members. The other two sections of the first and second strings are clamped between the other wheel and the other clamping member, not allowing adjustment of the spacing between the inner ends of the first and second positioning members.

On the other hand, when the wheels are located adjacent to the second openings of the clamping members, the two sections of the first and second strings are not clamped between one of the wheels and one of the clamping members. The other two sections of the first and second strings are not clamped between the other wheel and the other clamping member, allowing adjustment of the spacing between the inner ends of the first and second positioning members.

The present invention will become clearer in light of the following detailed description of illustrative embodiments of this invention described in connection with the drawings.

DESCRIPTION OF THE DRAWINGS

The illustrative embodiments may best be described by reference to the accompanying drawings where.

Figure 1:
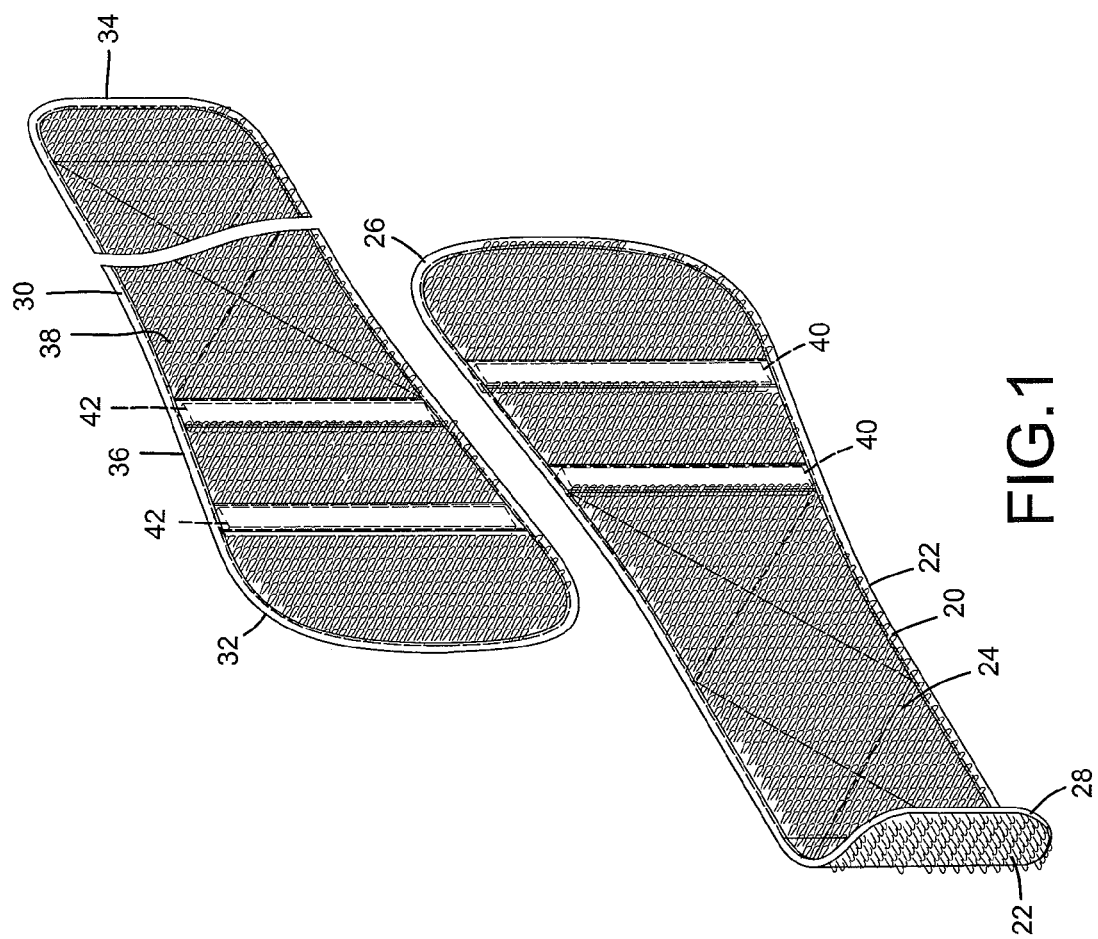
FIG. 1 shows an exploded, perspective view of two bands of a waist pad.
Figure 2:
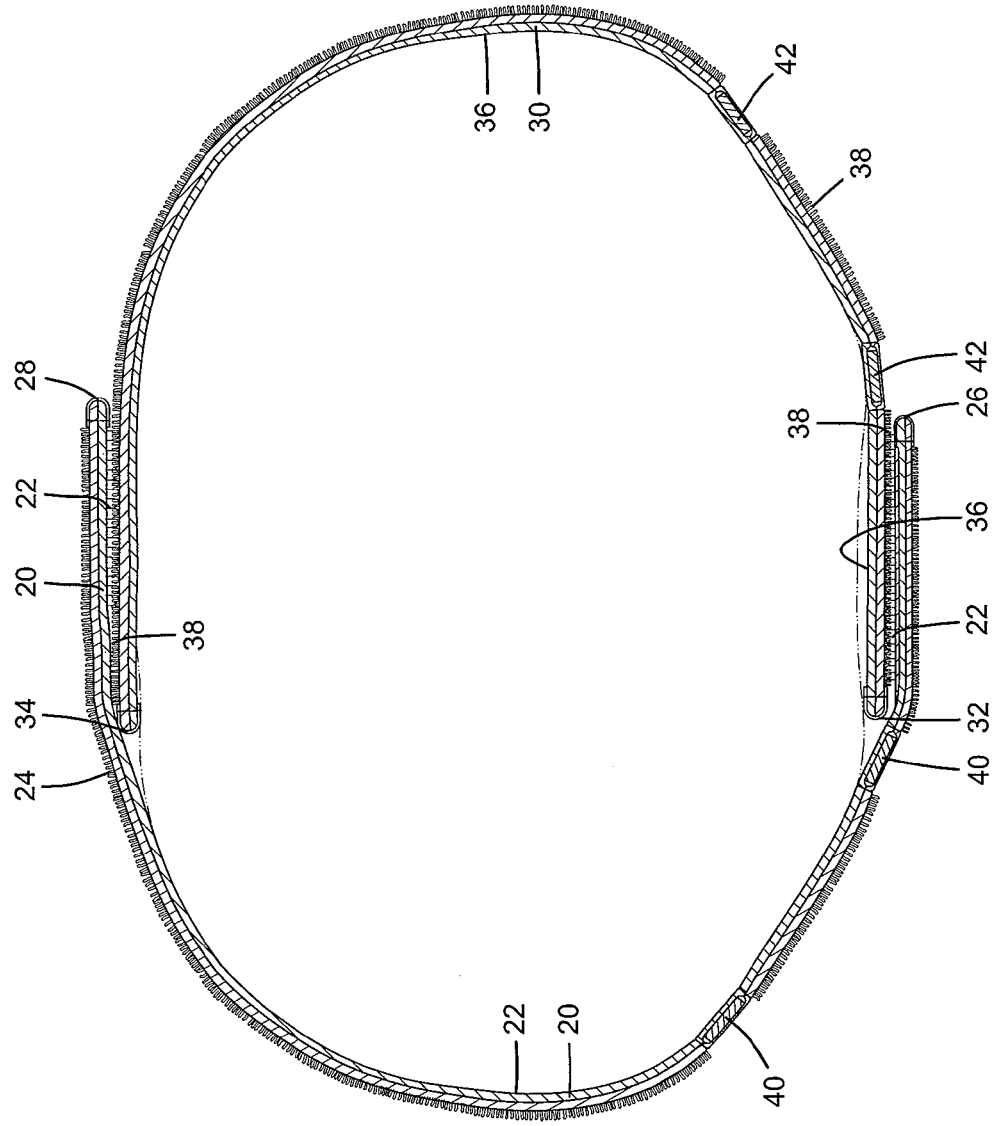
FIG. 2 shows a cross sectional view of the bands of FIG. 1 after assembly, with the bands wound around a waist of a user.
Figure 3:
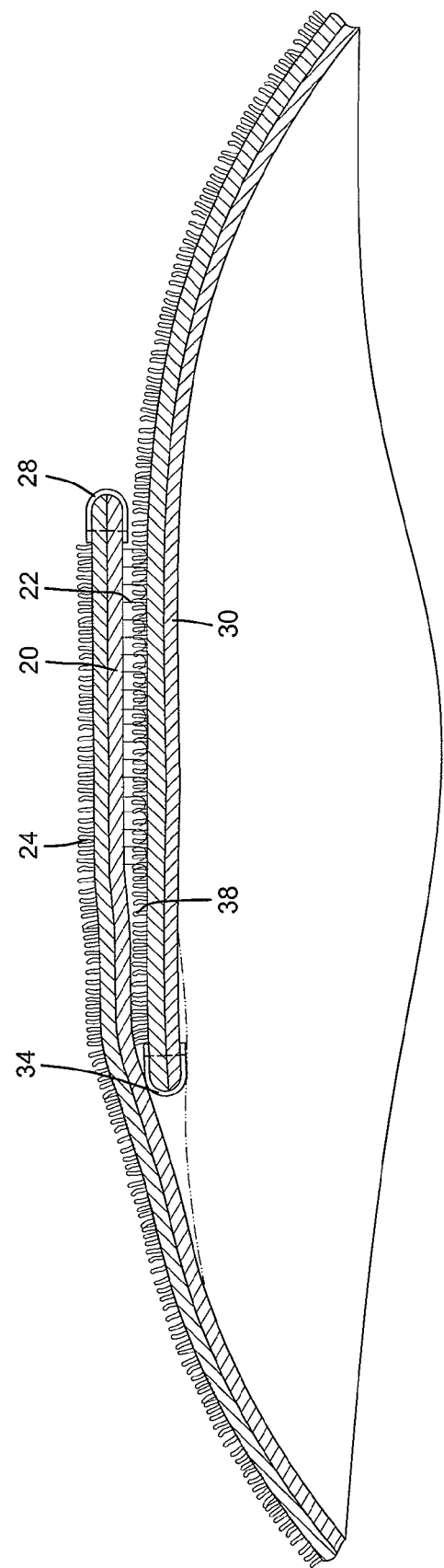
FIG. 3 shows an enlarged view of two ends respectively of the bands shown in FIG. 2.
Figure 4:
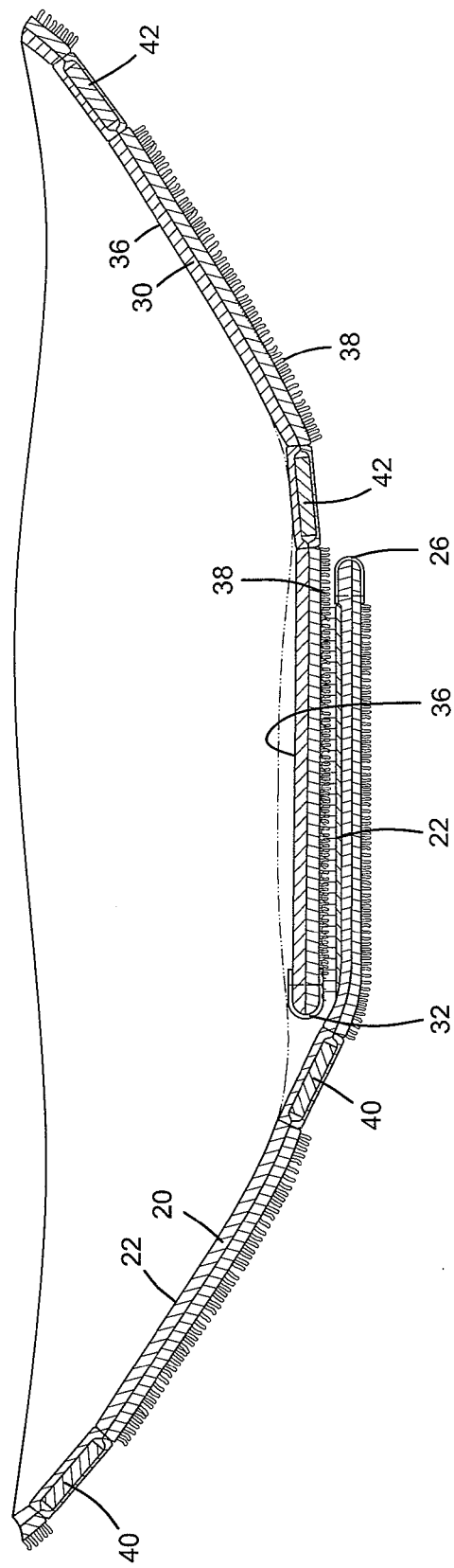
FIG. 4 shows an enlarged view of another two ends respective of the bands shown in FIG. 2.

All figures are drawn for ease of explanation of the basic teachings only; the extensions of the figures with respect to number, position, relationship, and dimensions of the parts to form the illustrative embodiments will be explained or will be within the skill of the art after the following teachings have been read and understood. Further, the exact dimensions and dimensional proportions to conform to specific force, weight, strength, and similar requirements will likewise be within the skill of the art after the following teachings have been read and understood.

Where used in the various figures of the drawings, the same numerals designate the same or similar parts. Furthermore, when the terms "first", "second", "third", "fourth", "lower", "upper", "top", "bottom", "end", "section", "vertical", "spacing", "length", and similar terms are used herein, it should be understood that these terms have reference only to the structure shown in the drawings as it would appear to a person viewing the drawings and are utilized only to facilitate describing the illustrative embodiments.

DETAILED DESCRIPTION OF THE INVENTION

With reference to FIGS. 1-7, a waist pad 2 according to the present invention includes a band unit 10 and a connecting assembly 12. Band unit 10 includes air-permeable first and second bands 20 and 30. First band 20 includes an engagement end 26 and a free end 28. First band 20 further includes an abutment face 22 and an engagement face 24 opposite to the abutment face 22, with each of abutment face 22 and engagement face 24 extending from engagement end 26 to free end 28. A plurality of hooks is provided on abutment face 22 of first band 20 at abutment end 26 and free end 28. A plurality of loops is provided on engagement face 24 of first band 20. A plurality of first supports 40 is fixed to engagement face 24 of first band 20 and located adjacent to engagement end 26 of first band 20. Each first support 40 is an elastic, elongated plastic.

Second band 30 includes an engagement end 32 and a free end 34. Second band 30 further includes an abutment face 36 and an engagement face 38 opposite to the abutment face 36, with each of abutment face 36 and engagement face 38 extending from engagement end 32 to free end 34. A plurality of loops is provided on engagement face 38 of second band 30. A plurality of second supports 42 is fixed to engagement face 38 of second band 30 and located adjacent to engagement end 32 of second band 30. Each second support 42 is an elastic, elongated plastic.

Engagement end 26 of first band 20 is detachably engaged with engagement face 38 of second band 30 at engagement end 32. When worn on a waist of a user, abutment face 22 of first band 20 and abutment face 36 of second band 30 abut the waist of the user, with the hooks on the abutment face 22 at the free end 28 of the first band 20 engaged with the loops on the engagement face 38 of the second band 30. Thus, the waist of the user is wrapped by band unit 10. Note that engagement end 26 of first band 20 is not engaged with engagement end 32 of second band 30 when band unit 10 is coupled with connecting assembly 12.

Figure 5:
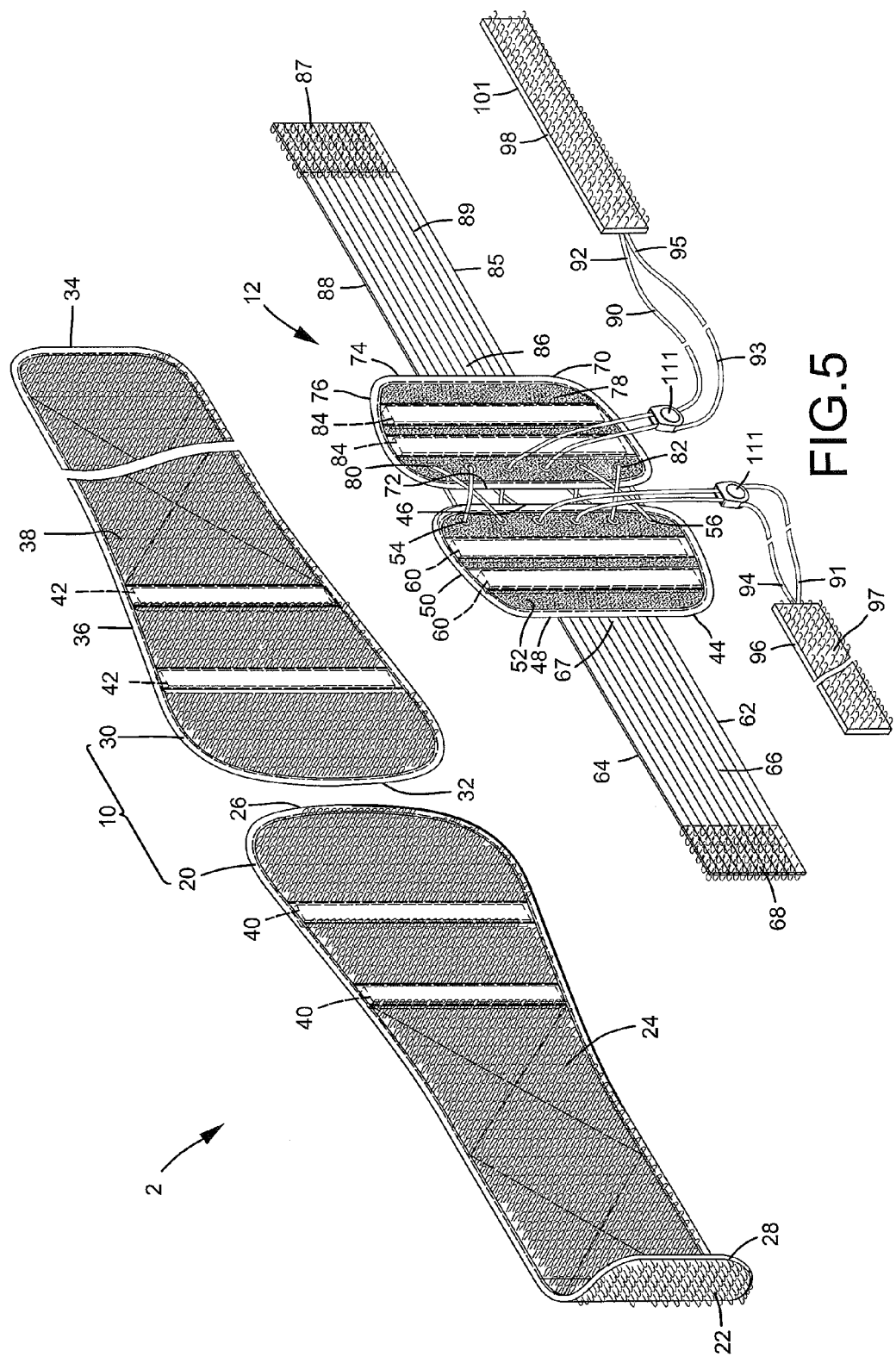
FIG. 5 shows an exploded, perspective view of the bands and a connecting assembly of the waist pad.
Figure 6:
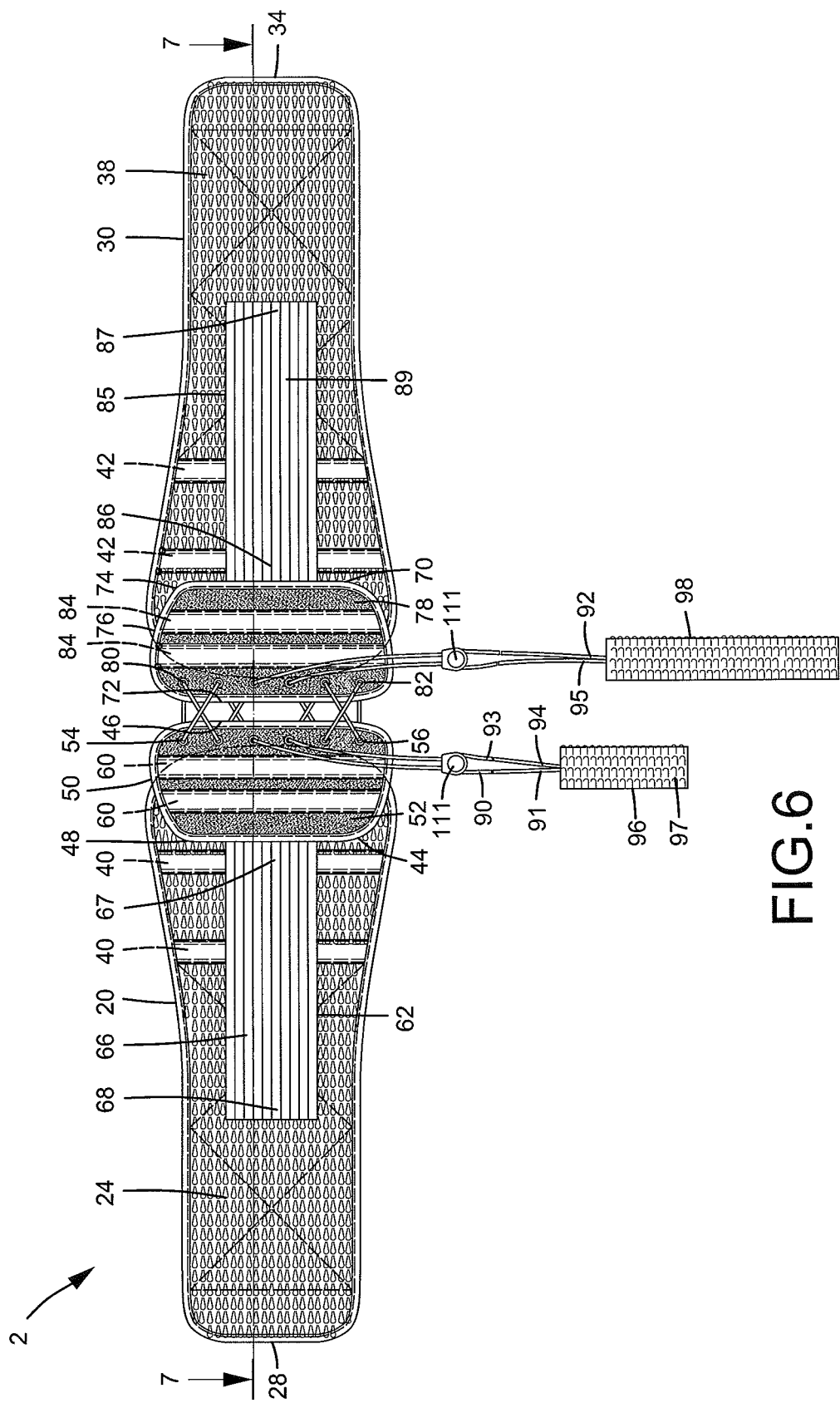
FIG. 6 shows a front view of the waist pad after assemblage.
Figure 7:
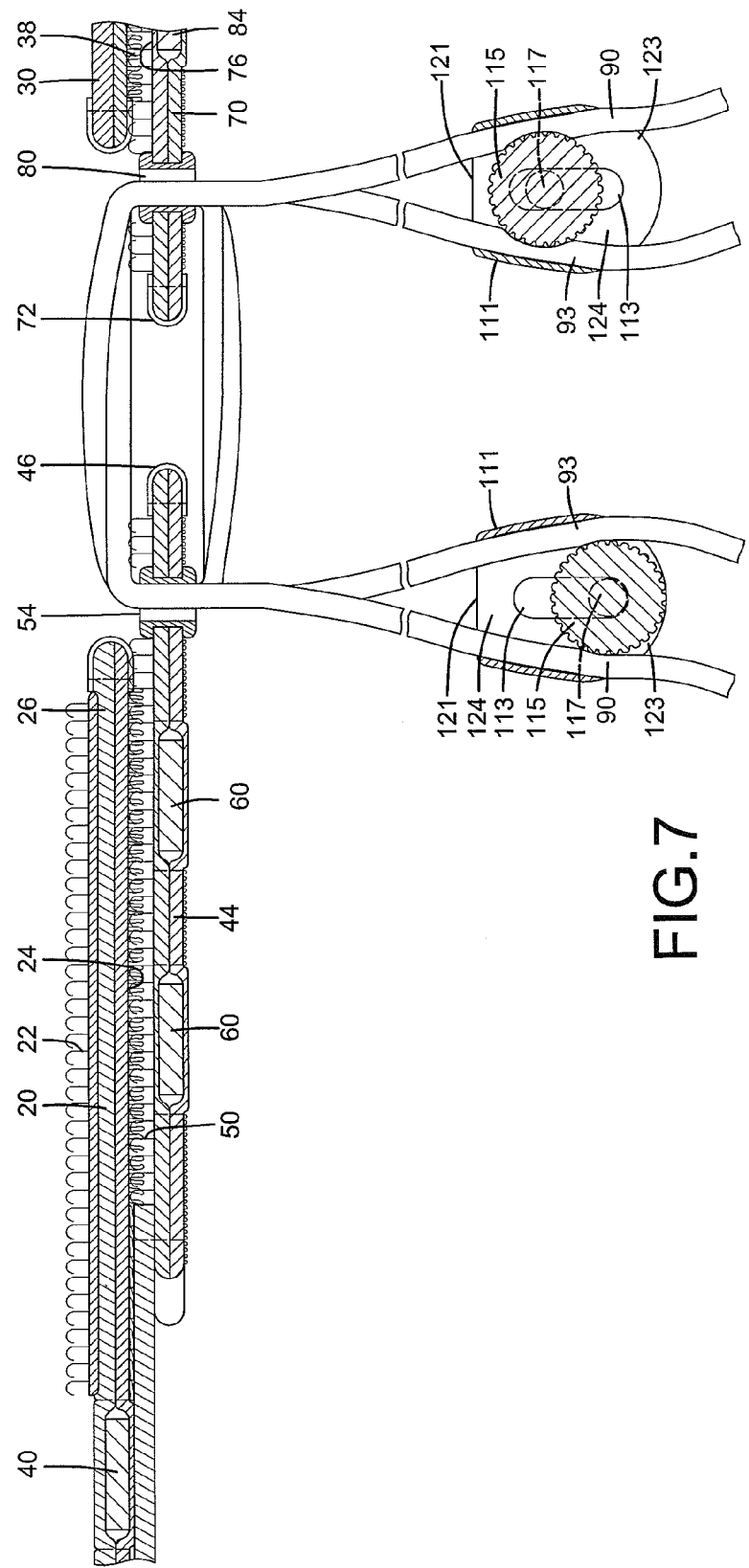
FIG. 7 shows a cross sectional view taken along section line 7-7 of FIG. 6.

With reference to FIGS. 5-7, connecting assembly 12 includes first and second positioning members 44 and 70 and first and second strings 90 and 93 extending through the first and second positioning members 44 and 70. First positioning member 44 includes an inner end 46 and an outer end 48 opposite to inner end 46. First positioning member 44 further includes a coupling face 50 and an outer face 52 opposite to coupling face 50, with each of coupling face 50 and outer face 52 extending from inner end 46 to outer end 48. Coupling face 50 includes a plurality of hooks. Three upper holes 54 and three lower holes 56 are defined in inner end 46 of first positioning member 44 and spaced from each other in a vertical direction. A plurality of third supports 60 is fixed to outer face 52 of first positioning member 44. Each third support 60 is an elastic, elongated plastic. Coupling face 50 of first positioning member 44 is detachably engaged with engagement face 24 at engagement end 26 of first band 20.

Second positioning member 70 includes an inner end 72 and an outer end 74 opposite to inner end 72. Second positioning member 70 further includes a coupling face 76 and an outer face 78 opposite to coupling face 76, with each of coupling face 76 and outer face 78 extending from inner end 72 to outer end 74. Coupling face 76 includes a plurality of hooks. Three upper holes 80 and three lower holes 82 are defined in inner end 72 of second positioning member 70 and spaced from each other in the vertical direction. A plurality of fourth supports 84 is fixed to outer face 78 of second positioning member 70. Each fourth support 84 is an elastic, elongated plastic. Coupling face 76 of second positioning member 70 is detachably engaged with engagement face 38 at engagement end 32 of second band 30. Inner end 72 of second positioning member 70 is spaced from inner end 46 of first positioning member 44. Each upper hole 80 of second positioning member 70 is aligned with a corresponding upper hole 54 of first positioning member 44. Each lower hole 82 of second positioning member 70 is aligned with a corresponding lower hole 56 of first positioning member 44.

Inner ends 46 and 72 of first and second positioning members 44 and 70 are tied to each other by first and second strings 90 and 93. First string 90 includes first and second ends 91 and 92. First end 91 of first string 90 is extended through the uppermost upper hole 54 of first positioning member 44, the middle upper hole 80 of second positioning member 70, and the bottommost upper hole 54 of first positioning member 44. Second end 92 of first string 90 is extended through the uppermost upper hole 80 of second positioning member 70, the middle upper hole 54 of first positioning member 44, and the bottommost upper hole 80 of second positioning member 70. Thus, first string 90 is extended through upper sections of inner ends 46 and 72 of first and second positioning members 44 and 70 in a crisscross manner. When first and second ends 91 and 92 of first string 90 are pulled, inner ends 46 and 72 of first and second positioning members 44 and 70 move towards each other, reducing a spacing between inner ends 46 and 72.

Second string 93 includes first and second ends 94 and 95. First end 94 of second string 93 is extended through the uppermost lower hole 56 of first positioning member 44, the middle lower hole 82 of second positioning member 70, and the bottommost lower hole 56 of first positioning member 44. Second end 95 of second string 93 is extended through the bottommost lower hole 82 of second positioning member 70, the middle lower hole 56 of first positioning member 44, and the uppermost lower hole 82 of second positioning member 70. Thus, second string 93 is extended through lower sections of inner ends 44 and 72 of first and second positioning members 44 and 70 in a crisscross manner. When first and second ends 94 and 95 of second string 93 are pulled, inner ends 46 and 72 of first and second positioning members 44 and 70 move towards each other, reducing a spacing between inner ends 46 and 72.

Waist pad 2 further includes two clamping members 111, with each clamping member 111 including a compartment 124 having a first opening 121 and a second opening 123 larger than first opening 121. Compartment 124 includes a wall having a sliding groove 113 in communication with outside. Two sections respectively of first and second strings 90 and 93 are extended into compartment 124 of one of clamping members 111 via first opening 121 and then exit clamping member 111 via second opening 123. Another two sections respectively of first and second strings 90 and 93 are extended into compartment 124 of the other clamping member 111 via first opening 121 and then exit clamping member 111 via second opening 123. Thus, first and second ends 91, 92 and 94, 95 of first and second strings 90 and 93 are located outside of clamping members 111.

A wheel 115 is rotatably mounted in compartment 124 of each clamping member 111. Each wheel 115 includes a pivot 117 formed on a side thereof and extending into sliding groove 113 of a corresponding clamping member 111. Each pivot 117 is slideable in the corresponding sliding groove 113 and has an end located outside of a corresponding clamping member 111. Thus, each pivot 117 is manually operable to move the corresponding wheel 115 between first and second openings 121 and 123 of a corresponding clamping member 111. When wheel 115 is in a location adjacent to first opening 121 (see the right clamping member 111 in FIG. 7), two sections respectively of first and second strings 90 and 93 are securely clamped between wheel 115 and a corresponding clamping member 111. On the other hand, when wheel 115 is in a location adjacent to second opening 123 (see the left clamping member 111 in FIG. 7), two sections respectively of first and second strings 90 and 93 are not clamped between wheel 115 and a corresponding clamping member 111.

Waist pad 2 further includes a first fixing member 96 having a coupling face 97 with a plurality of hooks. First ends 91 and 94 of first and second strings 90 and 93 are fixed to an end of first fixing member 96.

Waist pad 2 further includes a second fixing member 98 having an engagement face 101. Coupling face 99 has a plurality of hooks. Engagement face 101 has a plurality of loops. Second ends 92 and 95 of first and second strings 90 and 93 are fixed to an end of second fixing member 98.

Waist pad 2 further includes a first elastic strap 62 having a connection end 67 and an engagement end 68. Connection end 67 of first elastic strap 62 is fixed to outer end 48 of first positioning member 44. First elastic strap 62 further includes a coupling face 64 and an outer face 66 opposite to coupling face 64, with each of coupling face 64 and outer face 66 extending from connection end 67 to engagement end 68. Coupling face 64 includes a plurality of hooks at engagement end 68. Coupling face 64 at engagement end 68 is detachably engaged with engagement face 24 of first band 20.

Waist pad 2 further includes a second elastic strap 85 having a connection end 86 and an engagement end 87. Connection end 86 of second elastic strap 85 is fixed to outer end 74 of second positioning member 70. Second elastic strap 85 further includes a coupling face 88 and an outer face 89 opposite to coupling face 88, with each of coupling face 88 and outer face 89 extending from connection end 86 to engagement end 87. Coupling face 88 includes a plurality of hooks at engagement end 87. Coupling face 88 at engagement end 87 is detachably engaged with engagement face 38 of second band 30.

After assemblage of first and second bands 20 and 30 with first and second positioning members 44 and 70, if the spacing between engagement ends 26 and 32 of first and second bands 20 and 30 is large, the spacing between free ends 28 and 34 of first and second bands 20 and 30 is also large, which is suitable for a user having a large waist. On the other hand, if the spacing between engagement ends 26 and 32 of first and second bands 20 and 30 is small, the spacing between free ends 28 and 34 of first and second bands 20 and 30 is also small, which is suitable for a user having a small waist.

Figure 8:
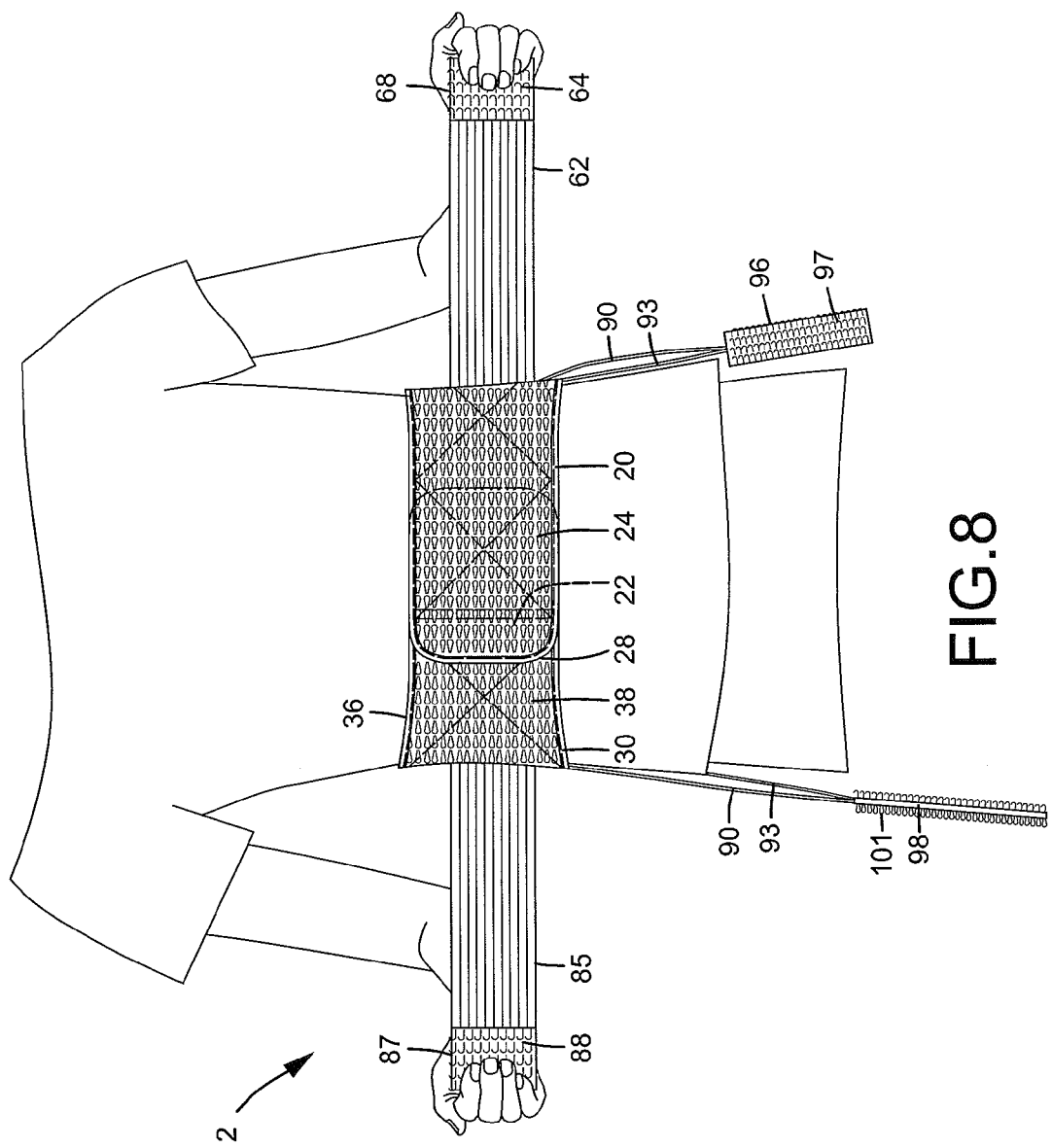
FIG. 8 illustrates use of the waist pad on a waist of a user, with the user pulling two elastic bands.

Now that the basic construction of waist pad 2 has been explained, the operation and some of the advantages of waist pad 2 can be set forth and appreciated. In particular, for the sake of explanation, it will be assumed that inner ends 46 and 72 of first and second positioning members 44 and 70 are spaced from each other by a spacing, with the first and second bands 20 and 30 wrapping the waist of the user, with abutment faces 22 and 36 of first and second bands 20 and 30 abutting the waist of the user, with the first and second positioning members 44 and 70 located at the back of the waist of the user. Thus, waist pad 2 wraps around the waist of the user (FIG. 8).

Figure 9:
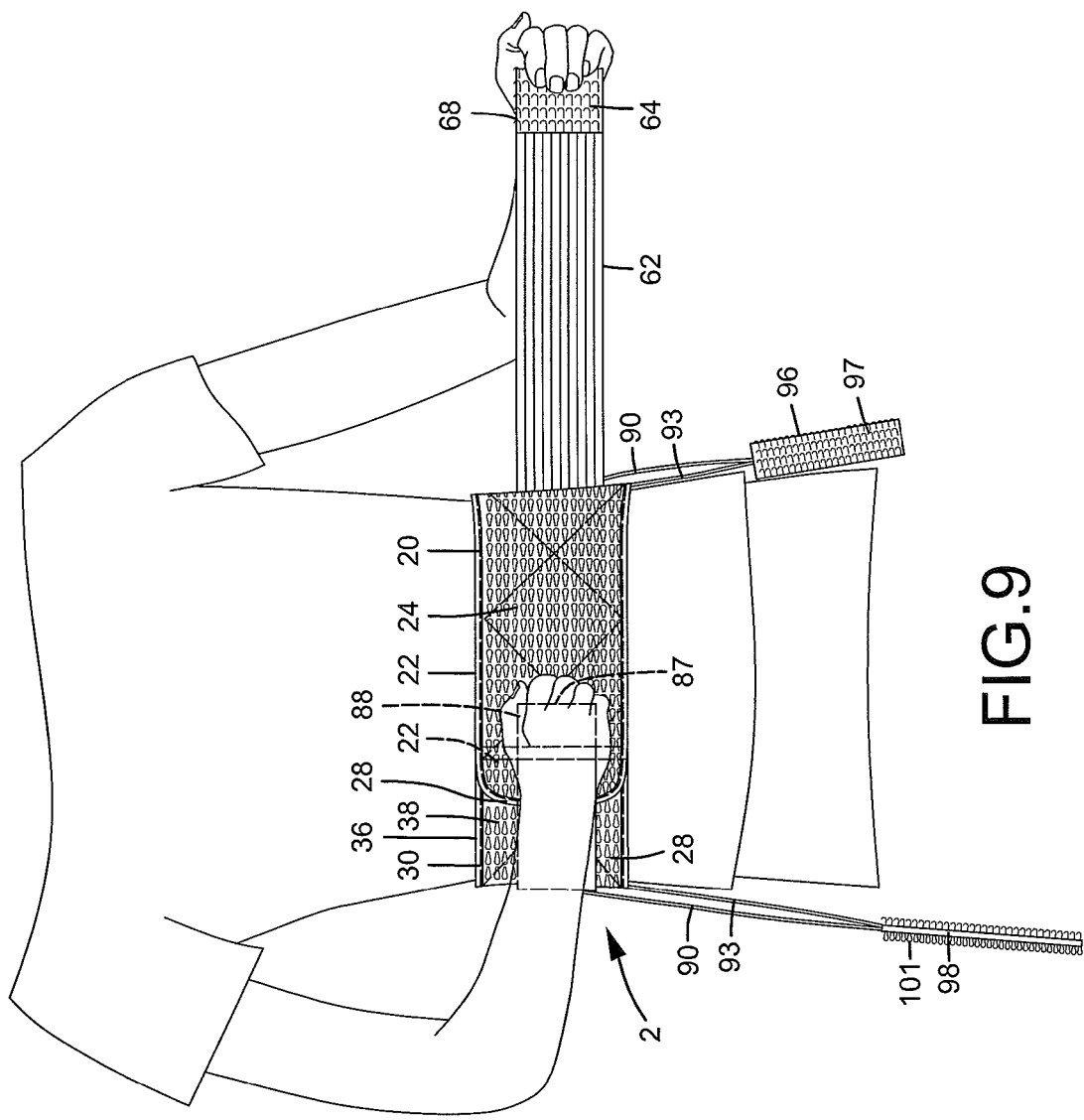
FIG. 9 shows a view similar to FIG. 8, illustrating adjustment of tightness of the waist pad.
Figure 10:
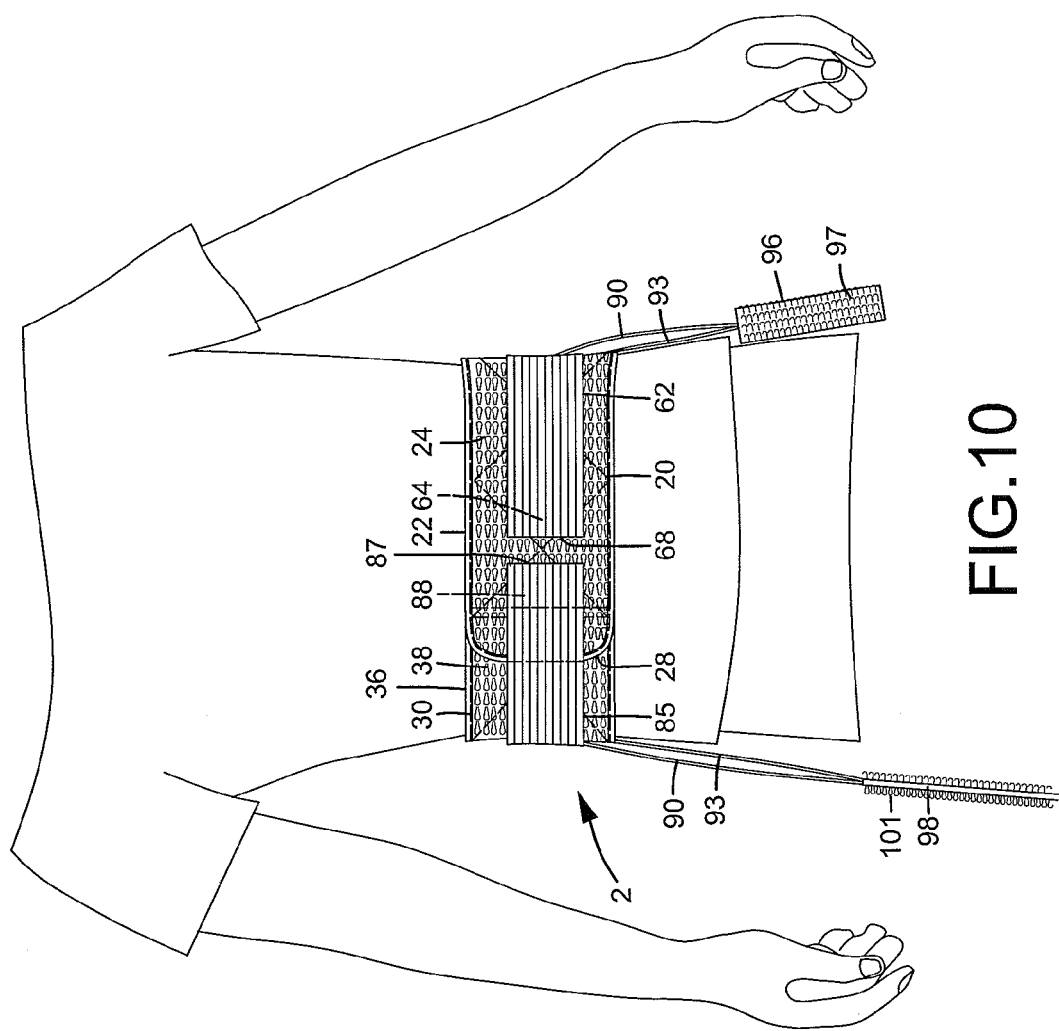
FIG. 10 shows a front view of the waist pad of FIG. 9 after adjustment.

First and second elastic straps 62 and 85 can be operated to increase the tightening force to the waist of the user. Specifically, when first and second elastic straps 62 and 85 are pulled, an elastic force is imparted to reliably position coupling faces 64 and 88 at engagement ends 68 and 87 of first and second elastic bands 62 and 85 to engagement faces 24 and 38 of first or second band 20 or 30 (FIGS. 9 and 10). The tightening force imparted to the waist of the user is increased by the elastic force resulting from pulling first and second elastic straps 62 and 85. The elastic force varies according to the extent of elongation of first and second elastic straps 62 and 85. Thus, engagement ends 68 and 87 of first and second elastic straps 62 and 85 can be positioned to different locations of engagement faces 24 and 38 of first or second band 20 or 30, allowing rapid adjustment of the tightening force of first and second elastic straps 62 and 85.

Figure 11:
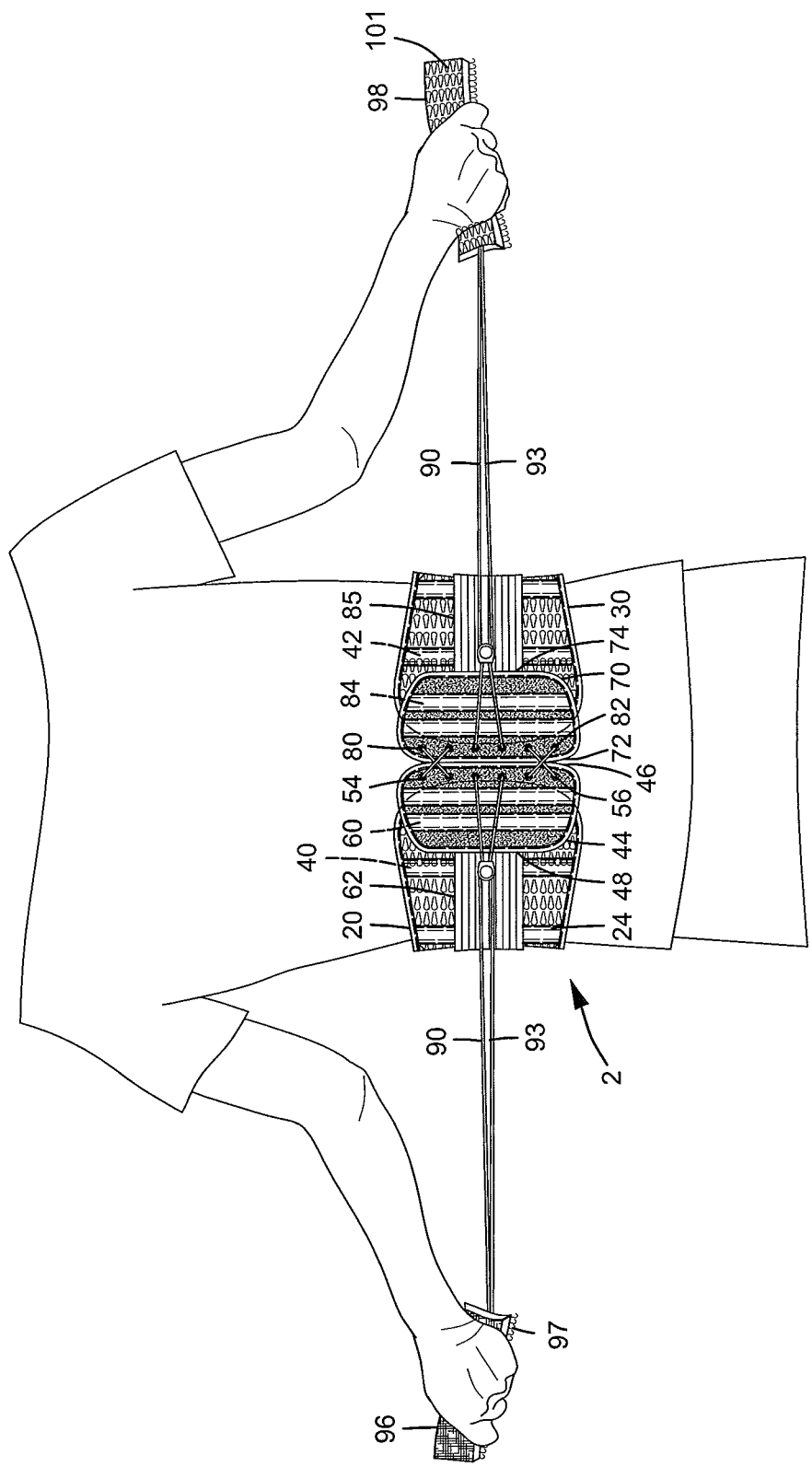
FIG. 11 shows a rear view of the waist pad of FIG. 10, with the user pulling two strings to shorten a spacing between two positioning members by pulling first and second fixing members.
Figure 12:
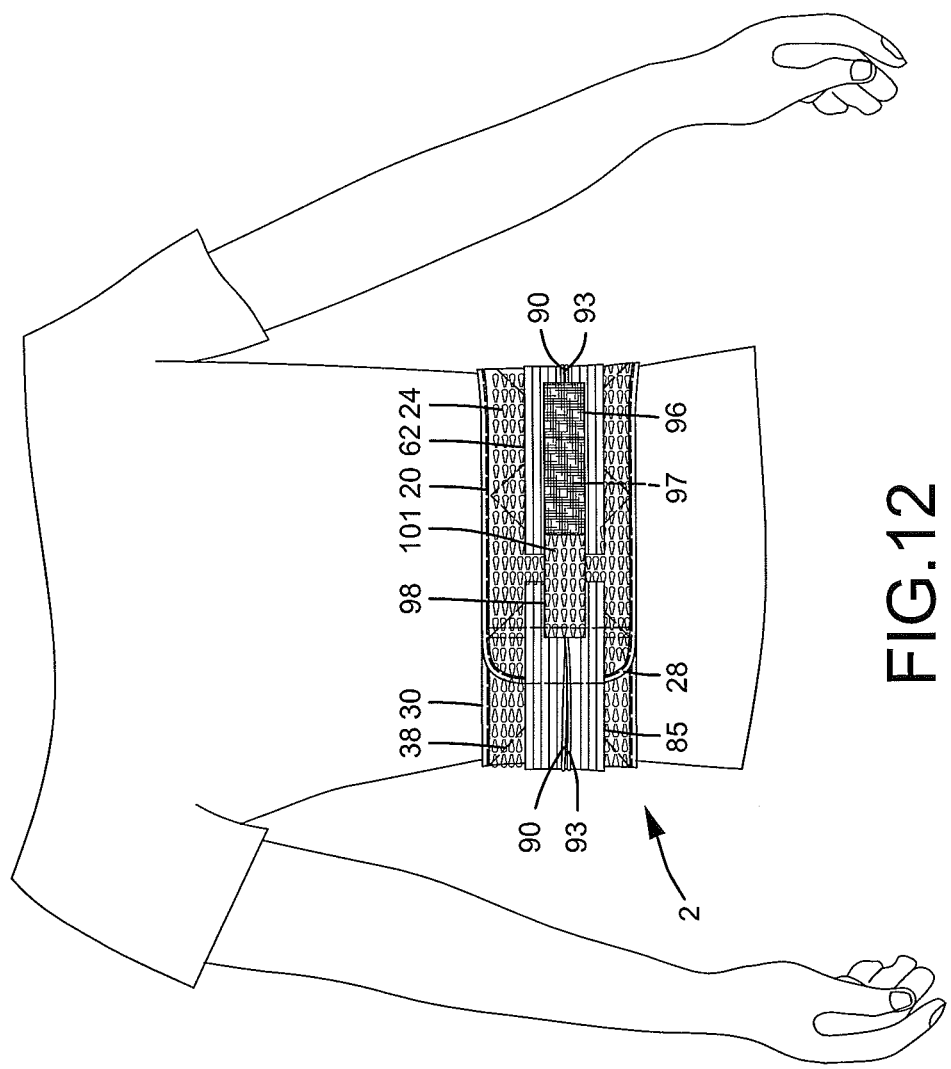
FIG. 12 shows a front view of the waist pad of FIG. 10 after pulling the strings, with the first fixing member engaged with the second fixing member after adjustment of the spacing.

After pulling and engagement of first and second elastic bands 62 and 85, first and second strings 90 and 93 can be pulled to further increase the tightening force of waist pad 2. Specifically, the waist of the user can be further tightened by pulling first and second fixing members 96 and 98 to tighten first and second strings 90 and 93 (FIG. 11). Then, coupling face 97 of first fixing member 96 is engaged with engagement face 101 of second fixing member 98 (FIG. 12), Thus, the spacing between inner ends 46 and 72 of first and second positioning members 44 and 70 is fixed while retaining the tightening effect.

Figure 13:
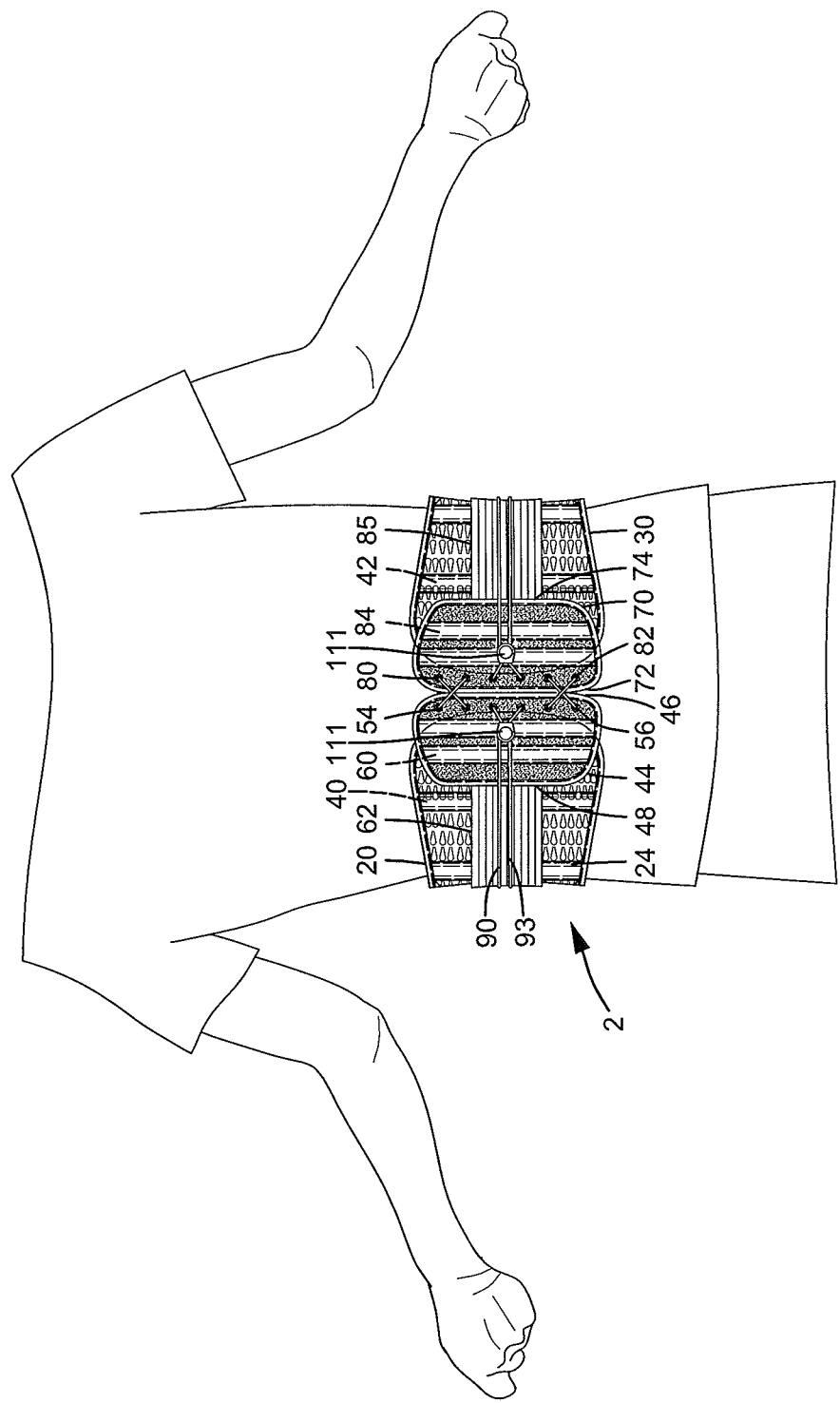
FIG. 13 shows a rear view of the waist pad of FIG. 12, with each of two clamping members moved to a position adjacent to an outer side of a corresponding positioning member.

In addition to using first and second fixing members 96 and 98 to fix the spacing between inner ends 46 and 72 of first and second positioning members 44 and 70, clamping members 111 can be used to increase the positioning effect of first and second strings 90 and 93, avoiding an increase of the spacing between inner ends 46 and 72 of first and second positioning members 44 and 70 due to loosening of first and second strings 90 and 93. Specifically, each wheel 115 is moved towards second opening 123 of a corresponding clamping member 111 to release first and second strings 90 and 93. Each clamping member 111 is then moved towards outer face 52, 78 of a corresponding one of first and second positioning members 44 and 70 (FIG. 13). Each wheel 115 is then moved towards first opening 121 of a corresponding clamping member 111 to clamp first and second strings 90 and 93. Thus, first and second positioning members 44 and 74 can not move in a direction increasing the spacing between inner ends 46 and 72, reliably fixing the spacing between inner ends 46 and 72.

In a case that minor adjustment of an overall length of waist pad 2 is required, first and second fixing members 96 and 98 is disengaged from each other, and clamping members 111 are moved away from each other such that first and second positioning members 44 and 70 can be moved away from each other to slightly adjust the overall length of waist pad 2. Next, clamping members 111 are moved towards outer faces 52 and 78 and then fixed, completing the minor adjustment.

The overall length of waist pad 2 can be adjusted according to the size of the waist of the user. Furthermore, with first and second bands 2 and 30 wrapped around the waist of the user, the tightening force imparted to the waist can be increased by pulling first and second elastic straps 62 and 85. Further, the tightening force imparted to the waist can be further increased by pulling first and second fixing members 96 and 98 to reduce the spacing between inner ends 46 and 72 of first and second positioning members 44 and 70. Thus, the tightening force can be easily adjusted according to needs.

Now that the basic teachings of waist pad 2 have been explained, many extensions and variations will be obvious to one having ordinary skill in the art. For example, waist pad 2 does not have to include second string 93, first positioning member 44 does not have to include lower holes 56, second positioning member 70 does not have to include lower holes 82. In this case, the spacing between inner ends 46 and 72 of first and second positioning members 44 and 70 is still reduced by pulling first string 90. Furthermore, waist pad 2 does not have to include clamping members 111, and first and second strings 90 and 93 can still be positioned by first and second fixing members 96 and 98. Further, first band 20 does not have to include first supports 40, second band 30 does not have to include second supports 42, first positioning member 44 does not have to include third supports 60, and second positioning member 70 does not have to include fourth supports 84.

Thus since the illustrative embodiments disclosed herein may be embodied in other specific forms without departing from the spirit or general characteristics thereof, some of which forms have been indicated, the embodiments described herein are to be considered in all respects illustrative and not restrictive. The scope is to be indicated by the appended claims, rather than by the foregoing description, and all changes which come within the meaning and range of equivalency of the claims are intended to be embraced therein.

The invention claimed is:

1. An adjustable waist pad comprising:
  a first band including an engagement end and a free end, with the first band further including an abutment face and an engagement face opposite to the abutment face, with each of the abutment face and the engagement face of the first band extending from the engagement end to the free end of the first band;
  a second band including an engagement end and a free end, with the second band further including an abutment face and an engagement face opposite to the abutment face, with each of the abutment face and the engagement face of the first band extending from the engagement end to the free end of the second band, with the abutment face at the free end of the first band detachably engaged with the engagement face of the second band;
  a first positioning member including an inner end and an outer end opposite to the inner end, with the first positioning member further including a coupling face and an outer face opposite to the coupling face, with each of the coupling face and the outer face extending from the inner end to the outer end of the first positioning member, with three upper holes defined in the inner end of the first positioning member and spaced from each other in a vertical direction, with the coupling face of the first positioning member detachably engaged with the engagement face at the engagement end of the first band;

a second positioning member including an inner end and an outer end opposite to the inner end, with the second positioning member further including a coupling face and an outer face opposite to the coupling face, with each of the coupling face and the outer face extending from the inner end to the outer end of the second positioning member, with three upper holes defined in the inner end of the second positioning member and spaced from each other in the vertical direction, with the coupling face of the second positioning member detachably engaged with the engagement face at the engagement end of the second band, with a spacing defined between the inner ends of the first and second positioning members, with each of the three upper holes of the second positioning member aligned with a corresponding one of the three upper holes of the first positioning member;

a first string including first and second ends, with the first end of the first string extended through an uppermost one of the three upper holes of the first positioning member, a middle one of the three upper holes of the second positioning member, and a bottommost one of the three upper holes of the first positioning member, with the second end of the first string extended through an uppermost one of the three upper holes of the second positioning member, a middle one of the three upper holes of the first positioning member, and a bottommost one of the three upper holes of the second positioning member;

a first elastic strap having a connection end and an engagement end, with the connection end of the first elastic strap fixed to the outer end of the first positioning member, with the first elastic strap further including a coupling face and an outer face opposite to the coupling face, with each of the coupling face and the outer face of the first elastic strap extending from the connection end to the engagement end of the first elastic strap, with the coupling face at the engagement end of the first elastic strap detachably engaged with the engagement face of the first band, providing a tightening force;

a second elastic strap having a connection end and an engagement end, with the connection end of the second elastic strap fixed to the outer end of the second positioning member, with the second elastic strap further including a coupling face and an outer face opposite to the coupling face of the second elastic strap, with each of the coupling face and the outer face of the second elastic strap extending from the connection end to the engagement end of the second elastic strap, with the coupling face at the engagement end of the second elastic strap detachably engaged with the engagement face of the second band, providing a tightening force;

a first fixing member fixed to the first end of the first string, with the first fixing member including a coupling face;

a second fixing member fixed to the second end of the first string, with the second fixing member including an engagement face detachably engaged with the coupling face of the first fixing member, wherein with the first and second bands wrapped around a waist of a user, the tightening force of the first and second bands is increased if the first and second ends of the first string are pulled to reduce the spacing between the inner ends of the first and second positioning members, with the first positioning member further including three lower holes defined in the inner end thereof and spaced from each other in the vertical direction, with the three lower holes of the first positioning member located below the three upper holes of the first positioning member, with the second positioning member further including three lower holes defined in the inner end thereof and spaced from each other in the vertical direction, with the three lower holes of the second positioning member located below the three upper holes of the second positioning member, with each of the three lower holes of the second positioning member aligned with a corresponding one of the three lower holes of the first positioning member;

a second string having first and second ends, with the first end of the second string extended through an uppermost one of the three lower holes of the first positioning member, a middle one of the three lower holes of the second positioning member, and a bottommost one of the three lower holes of the first positioning member, with the second end of the second string extended through a bottommost one of the three lower holes of the second positioning member, a middle one of the three lower holes of the first positioning member, and an uppermost one of the three lower holes of the second positioning member, with the first end of the second string fixed to the first fixing member, with the second end of the second string fixed to the second fixing member;

wherein with the first and second bands wrapped around the waist of the user, the tightening force of the first and second bands is increased if the first and second ends of the second string are pulled to reduce the spacing between the inner ends of the first and second positioning members;

two clamping members, with each of the two clamping members including a compartment having a first opening and a second opening larger than the first opening, with the compartment including a wall having a sliding groove; and two wheels, with each of the two wheels rotatably mounted in the compartment of one of the two clamping members, with each of the two wheels including a pivot formed on a side thereof and extending into the sliding groove of the one of the two clamping members, with the pivot of each of the two wheels slideable in the sliding groove to move the wheel between the first and second openings, with two sections respectively of the first and second strings extending through the compartment of the one of the two clamping members, with another two sections respectively of the first and second strings extending through the compartment of another of the two clamping members, wherein with the two wheels located adjacent to the first openings of the two clamping members, the two sections of the first and second strings are clamped between one of the two wheels and one of the two clamping members, the other two sections of the first and second strings are clamped between another of the two wheels and the other of the two clamping members, not allowing adjustment of the spacing between the inner ends of the first and second positioning members, and wherein with the two wheels located adjacent to the second openings of the two clamping members, the two sections of the first and second strings are not clamped between the one of the two wheels and the one of the two clamping members, the other two sections of the first and second strings are not clamped between the other of the two wheels and the other of the two clamping members, allowing adjustment of the spacing between the inner ends of the first and second positioning members.

2. The adjustable waist pad as claimed in claim 1, with a first support fixed to the engagement face of the first band and located adjacent to the engagement end of the first band, with a second support fixed to the engagement face of the second band and located adjacent to the engagement end of the second band, with a third support fixed to the outer face of the first positioning member, and with a fourth support fixed to the outer face of the second positioning member.

* * * * *